United States Patent
Chang et al.

(10) Patent No.: US 11,155,530 B2
(45) Date of Patent: Oct. 26, 2021

(54) UREA-OXAZIRIDINES

(71) Applicant: The Regents of the University of California, Oakland, CA (US)

(72) Inventors: Christopher J. Chang, Berkeley, CA (US); F. Dean Toste, Berkeley, CA (US); Alec H. Christian, Berkeley, CA (US); Patti Zhang, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/163,578

(22) Filed: Feb. 1, 2021

(65) Prior Publication Data

US 2021/0155600 A1    May 27, 2021

Related U.S. Application Data

(63) Continuation of application No. PCT/US2019/046251, filed on Aug. 13, 2019.

(60) Provisional application No. 62/718,235, filed on Aug. 13, 2018.

(51) Int. Cl.
*C07D 327/02* (2006.01)
*C07D 411/06* (2006.01)

(52) U.S. Cl.
CPC .......... *C07D 327/02* (2013.01); *C07D 411/06* (2013.01)

(58) Field of Classification Search
CPC ........................... C07D 411/06; C07D 327/02
See application file for complete search history.

(56) References Cited

FOREIGN PATENT DOCUMENTS

WO    WO-2018089951 A1 *  5/2018   ........... A61K 47/643

OTHER PUBLICATIONS

Christian et al. ChemRxiv2019, pp. 1-7 (Year: 2019).*
Armstrong et al. Tetrahedron Letters 2003, 44, 5335-5338 (Year: 2003).*

* cited by examiner

*Primary Examiner* — Matthew P Coughlin
(74) *Attorney, Agent, or Firm* — Richard Aron Osman

(57) ABSTRACT

Chemoselective conjugation is achieved through redox reactivity by reacting an N-transfer oxidant with a thioether substrate in a redox reaction in an aqueous environment to form a conjugation product. In embodiments, Redox-Activated Chemical Tagging (ReACT) strategies for methionine-based protein functionalization. Oxaziridine (Ox) compounds serve as oxidant-mediated reagents for direct functionalization by converting methionine to the corresponding sulfimide conjugation product.

10 Claims, No Drawings

UREA-OXAZIRIDINES

This invention was made with government support under Grant Numbers GM118190 and GM079465 awarded by the National Institutes of Health. The government has certain rights in the invention.

INTRODUCTION

In WO2018089951 we disclosed chemoselective conjugation by reacting an N-transfer oxidant with a thioether substrate in a redox reaction in an aqueous environment to form a conjugation product. In an embodiment, a Redox-Activated Chemical Tagging (ReACT) strategy uses methionine-based protein functionalization wherein oxaziridine (Ox) compounds serve as oxidant-mediated reagents for direct functionalization by converting methionine to the corresponding sulfimide conjugation product. Here we disclose novel urea-oxaziridine scaffolds.

SUMMARY OF THE INVENTION

The invention provides methods and compositions for chemoselective redox conjugation to thioether substrates, and compounds and compositions comprising the conjugated substrates. The methods (Redox Activated Chemical Tagging, or ReACT) generally comprise reacting an N-transfer oxidant with a thioether substrate in a redox reaction in an aqueous environment to form a conjugation product. The invention provides novel N-transfer oxidants, which comprise a reactive oxaziridine group which reacts with at least one of the one or more thioether moieties on the target molecule, wherein the conjugation product comprises a resultant sulfimide on the target molecule.

The oxaziridine's reactivity with methionine—to give a desired sulfimine or undesired sulfoxide product—is dependent on the urea functionality in the oxaziridine structure. This we determined through multivariate linear regression modeling and analysis of empirical data. Additional stability tests of the desired sulfimine products were found to have a correlation with the urea's structure. Compounds have been synthesized to install a wide variety of different functional groups onto the scaffold for biological testing and chemical modeling.

In an aspect the invention provides an N-transfer oxidant compound of formula A:

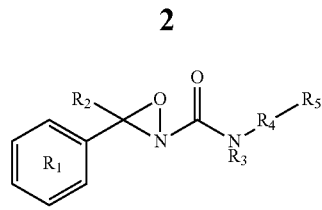

wherein NR is selected from:

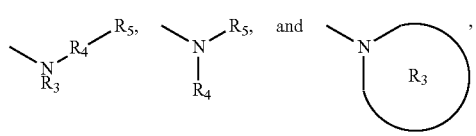

to obtain formulas I, II and III, respectively (below).
In an aspect the invention provides an N-transfer oxidant compound of formula I:

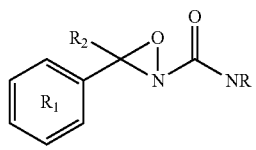

wherein:
R1 is optionally substituted C5, C6 or C8 aryl or heteroaryl (pyrrolyl, furanyl, phenyl, pyridinyl, naphthyl, etc.)
R2 is H or optionally substituted C1-C6 alkyl (particularly C1-C4 alkyl, e.g. Me, CF3, tBu, etc.)
R3 is H or optionally substituted C1-C6 alkyl (Me, tBu, cylcohexyl, etc.)
R4 is an optionally substituted methylene bridge or a bond; and
R5 is poly-(di- or tri-)substituted methyl or poly-(di- or tri-)substituted silyl.

In embodiments:
R1 is optionally substituted phenyl;
R2 is H;
R3 is H;
R4 is a bond; and/or
R5 is trisubstituted methyl.
R5 is trisubstituted with substituents independently selected from C1-C4 hydrocarbyl, C1-C4 hydrocarbyloxy, or C1-C4 hydrocarbyloxy-substituted C1-C4 hydrocarbyl, particularly wherein each hydrocarbyl is independently methyl, methoxy, methyoxymethyl, propynyl or propynyloxymethyl;
R5 is —C(CH3)3, —C(CH3)2(CH2OCH3), —C(CH3)(CH2OCH3)2, —C(CH2OCH3)3, —C(CH3)2(CCH), or —C(CH3)2(CH2OCCH); and/or
the compound is compound 11, 21, 23, 28, 33-35 or 37-50.

In an aspect the invention provides an N-transfer oxidant compound of formula II:

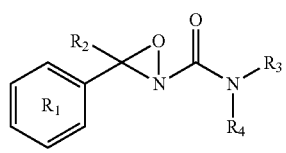

wherein:
R1 is optionally substituted C5, C6 or C8 aryl or heteroaryl (pyrrolyl, furanyl, phenyl, pyridinyl, naphthyl, etc.)
R2 is H or optionally substituted C1-C6 alkyl (particularly C1-C4 alkyl, e.g. Me, CF3, tBu, etc.); and
R3 and R4 are independently optionally substituted C1-C6 hydocarbyl, and optionally joined in an optionally substituted pyrrolidine or piperidine.

In embodiments:
R1 is optionally substituted phenyl;
R2 is H; and/or
R3 and R4 are independently optionally substituted C1-C6 alkyl, and optionally joined in an optionally substituted pyrrolidine or piperidine;
R3 and R4 are ethyl or cyclohexyl or joined forming pyrrolidine or piperidine; and/or
the compound is compound 9, 15-16, 30-31 or 51-54.
In an aspect the invention provides an N-transfer oxidant compound of formula III:

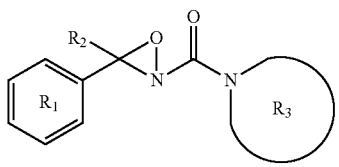

wherein:

R1 is optionally substituted C5, C6 or C8 aryl or heteroaryl (pyrrolyl, furanyl, phenyl, pyridinyl, naphthyl, etc.)

R2 is H or optionally substituted C1-C6 alkyl (particularly C1-C4 alkyl, e.g. Me, CF3, tBu, etc.); and R3 is optionally substituted pyrrolidine or piperidine.

In embodiments:

R1 is optionally substituted phenyl;

R2 is H; and/or

R3 is optionally substituted piperidine;

R3 is optionally para substituted piperidine; and/or the compound is compound 15, 16, 31, 51-54.

In an aspect the invention provides Redox Activated Chemical Tagging (ReACT), or a method of chemoselective conjugation comprising reacting a subject N-transfer oxidant with a thioether substrate in an aqueous environment to form a conjugation product comprising a resultant sulfimide.

In embodiments:

the thioether substrate is a methionine, particularly a methionine residue in a peptide, polypeptide, or protein, particularly wherein the protein is an enzyme, an antigenic protein, a chemokine, a cytokine, a cellular receptor, a cellular receptor ligand, or an antibody or active fragment thereof;

the method comprises contacting a methionine-containing peptide, polypeptide or protein with an oxaziridine in an aqueous environment, wherein the oxaziridine directly functionalizes the peptide, polypeptide, or protein by converting at least one methionine of the peptide, polypeptide, or protein to the corresponding sulfimide conjugation product; and/or the method further comprises stable isotope labeling with amino acid in cell culture (SILAC) or isotope coded affinity tag (ICAT).

In an aspect the invention provides a sulfimide compound of formula Ip, IIp, or IIIp:

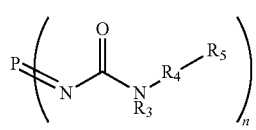

Ip

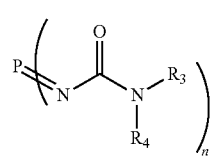

IIp

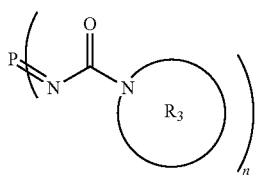

IIIp wherein P represents a peptide or protein linked to the indicated nitrogen via a sulfimide bond with the sulfur of methionine, wherein the peptide or protein has n sulfimide modified methionine residues, where n is 1 or more, including 1-20, 1-15, 1-10, 1-5, 1, 2, 3, 4 or 5, and R3, R4 and R5 are defined as in formulas I, II and III, respectively.

The invention encompasses all combination of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

The invention provides many commercial applications including therapeutic proteins functionalization based on methionine bioconjugation such as therapeutic protein PEGylation, antibody-drug conjugates, protein labeling for imaging and diagnosis, as well as other protein post translational modification; therapeutic polypeptides functionalization based on methionine bioconjugation such as polypeptide PEGylation, polypeptide-drug conjugates and other polypeptide post-translational modifications; therapeutic intervention based on methionine bioconjugation for protein function activation and/or inhibition; biomolecule functionalization based on thioether bioconjugation using oxaziridine compounds such as DNA, RNA, lipid and sugar bioconjugations In embodiments the present invention provides a highly selective, rapid, and robust methionine labeling methodology that is operable under a range of biocompatible reaction conditions using redox based reactivity without using electrophiles to label protein, thus avoiding a selectivity issue, and a resulting inconsistency of labeling in a protein drug; installation of various payloads onto proteins at well-defined positions and with excellent payload-target molecule conjugation efficiency due to the extremely high reactivity of the oxaziridine group with the thioether; etc.

Chemistry

A hydrocarbyl group is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which comprises 1-15 carbon atoms and optionally includes one or more heteroatoms in its carbon skeleton.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, isocyanate, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH2-CH2-CH2-CH2-. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, e.g. "haloalkoxy" refers to a haloalkyl group attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH2—CH2—O—CH3, —CH2—CH2—NH—CH3, —CH2—CH2—N(CH3)—CH3, —CH2—S—CH2—CH3, —CH2—CH2,—S(O)—CH3, —CH2—CH2—S(O)2—CH3, —CH=CH—O—CH3, —Si(CH3)3, —CH2—CH=N—OCH3, and —CH=CH—N(CH3)—CH3. Up to two heteroatoms may be consecutive, such as, for example, —CH2—NH—OCH3 and —CH2—O—Si(CH3)3.

Similarly, the term "heteroalkylene," by itself or as part of another substituent means a divalent radical derived from heteroalkyl, as exemplified by —CH2—CH2—S—CH2—CH2— and —CH2—S—CH2—CH2—NH—CH2—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "C1-4haloalkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "C1-4perhaloalkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —SiR'R"R'", —OC(O)R', —C(O)R', —CO2R', —CONR'R", —OC(O)NR'R", —NR"C(O)R', —NR'—C(O)NR"R'", —NR'—SO2NR'", —NR'CO2R', —NH—C(NH2)=NH, —NR'C(NH2) =NH, —NH—C(NH2)=NR', —S(O)R', —SO2R', —SO2NR'R", —NR"SO2R, —CN and —NO2, in a number ranging from zero to three, with those groups having zero, one or two substituents being particularly preferred. R', R" and R'" each independently refer to hydrogen, unsubstituted C1-8 alkyl and heteroalkyl, unsubstituted aryl, aryl substituted with one to three halogens, unsubstituted alkyl, alkoxy or thioalkoxy groups, or aryl-C1-4 alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF3 and —CH2CF3).

Preferred substituents for the alkyl and heteroalkyl radicals are selected from: —OR', =O, —NR'R", —SR', halogen, —SiR'R"R'", —OC(O)R', —C(O)R', —CO2R', —CONR'R", —OC(O)NR'R", —NR"C(O)R', —NR"CO2R', —NR'—SO2NR"R'", —S(O)R', —SO2R', —SO2NR'R", —NR" SO2R, —CN and —NO2, where R' and R" are as defined above. Further preferred substituents are selected from: —OR', =O, —NR'R", halogen, —OC (O)R', —CO2R', —CONR'R", —OC(O)NR'R", —NR"C (O)R', —NR"CO2R', —NR'—SO2NR"R'", —SO2R', —SO2NR'R", —NR"SO2R, —CN and —NO2.

Similarly, substituents for the aryl and heteroaryl groups are varied and selected from: halogen, —OR', —OC(O)R', —NR'R", —SR', —R', —CN, —NO2, —CO2R', —CONR'R", —C(O)R', —OC(O)NR'R", —NR"C(O)R', —NR"CO2R', —NR'—C(O)NR"R'", —NR'—SO2NR"R'", —NH—C(NH2)=NH, —NR'C(NH2)=NH, —NH—C (NH2)=NR', —S(O)R', —SO2R', —SO2NR'R", —NR"SO2R, —N3, —CH(Ph)2, C1-4 perfluoroalkoxy and C1-4 perfluoroalkyl, in a number ranging from zero to the total number of open valences on the aromatic ring system; and where R', R" and R'" are independently selected from hydrogen, C1-8 alkyl and heteroalkyl, unsubstituted aryl and heteroaryl, (unsubstituted aryl)-C1-4 alkyl and (unsubstituted aryl)oxy-C1-4 alkyl. When the aryl group is 1,2,3,4-tetrahydronaphthalene, it may be substituted with a substituted or unsubstituted C3-7 spirocycloalkyl group. The C3-7 spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R', —CN, —NO2, —CO2R', —CONR'R", —C(O)R', —OC(O)NR'R", —NR"C(O)R', —S(O)R', —SO2R', —SO2NR'R", —NR"SO2R, —N3, —CH(Ph)2, C1-4 perfluoroalkoxy and C1-4 perfluoroalkyl, where R' and R" are as defined above. Further preferred substituents are selected from: halogen, —OR', —OC(O)R', —NR'R", —R', —CN, —NO2, —CO2R', —CONR'R", —NR"C(O)R', —SO2R', —SO2NR'R", —NR"SO2R, C1-4 perfluoroalkoxy and C1-4 perfluoroalkyl.

The substituent —CO2H, as used herein, includes bioisosteric replacements therefore; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH2)q-U—, wherein T and U are independently —NH—, —O—, —CH2- or a single bond, and q is an integer of from 0 to 2. Alternatively, two of the substituents on adjacent atoms of the aryl or heteroaryl ring may optionally be replaced with a substituent of the formula -A—(CH2)r-B—, wherein A and B are independently —CH2-, —O—, —NH—, —S—, —S(O)—, —S(O)2-, —S(O)2NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH2)s-X—(CH2)t-, where s and t are independently integers of from 0 to 3, and X is —O—, —NR'—, —S—, —S(O)—, —S(O)2-, or —S(O)2NR'—. The substituent R' in —NR'— and —S(O)2NR'— is selected from hydrogen or unsubstituted C1-6 alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, optionally heteroatom C1-6 alkyl, substituted or unsubstituted, optionally heteroatom C2-6 alkenyl, substituted or unsubstituted, optionally heteroatom C2-6 alkynyl, or substituted or unsubstituted, optionally heteroatom C6-14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, isocyanate, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The term "peptide" as used herein refers to at least two amino acids joined by peptide bonds. A "polypeptide" refers to a short sequence of amino acids (less than 50), where the amino acids are connected to each other by peptide bonds. A peptide or polypeptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A peptide or polypeptide may be connected to another moiety by way of a peptide bond or some other type of linkage. A polypeptide is more than two amino acids in length and generally less than about 25 amino acids in length. The terms "peptide" and "oligopeptide" may be used interchangeably.

"Protein" generally refers to the sequence of amino acids comprising a polypeptide chain and that is greater than 50 amino acids in length. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g., Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The term "cytokine" as used herein means any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-b).

The term "receptor" as used herein refers to a molecule, typically composed primarily of protein, that binds to a cognate ligand and that is associated, or derived from, a cell, and usually one or more types of cellular membranes, and has as its main biological function the ability to bind a specific ligand or group of ligands, and, upon ligand binding, to mediate signal transduction, either directly or indirectly, in the cell. One type of receptor has three portions or domains, namely, an intracellular domain, an extracellular domain, and a transmembrane domain. In addition, the receptor typically has a sequence of about 5-25 amino acids at its amino terminus that serve to target the receptor to the proper membrane. These domains will vary in size and in function from receptor to receptor. Typically, the extracellular domain binds to one or more ligands, the transmembrane domain anchors the receptor into the membrane, and the intracellular domain perceives the binding of ligand and transmits a signal to the interior of the cell (the intracellular environment).

The term "chemokine" as used herein refers to a member of one of 4 different structural families, comprising over 50 ligands that interact with at least 17 different receptors These chemokine families, named according to the structure of a conserved cysteine-containing motif, are defined by the presence of either a C, a CC, a CXC, or a C'C at their amino terminus of the protein. The term "amino acid peptide", e.g. as used in describing compounds of formula II (including a compound of formula IIa) refers to the bonds within a protein or polypeptide, wherein the thioether containing substrate includes an amino acid peptide, e.g. is part of an amino acid residue of a polypeptide or protein, in a preferred embodiment, the thioether is within a methionine residue of a polypeptide or protein. As such, the substrate R4-S—R5 represents e.g. a thioether wherein R4 and R5 are alkyl groups, and the alkyl group of R5 is substituted at one carbon with both the —NHC(O)R, and —C(O)NHR' groups within a polypeptide or protein (e.g. where R is an additional peptide chain or a carboxyl terminus OH and R' is an additional peptide chain or an amino terminus H). It is also understood that the substrate may comprise a polypeptide or protein that has additional modifications, or may have additional methionine residues that can be reacted by the methods of the present invention as described herein.

An "active moiety" is a payload molecule as described in the present invention, wherein said moiety conjugated to e.g. a protein or polypeptide provides some activity. The activity of the moiety includes, but is not limited to, a biological activity (e.g. a pharmaceutically active moiety, such as a small molecule pharmaceutical or a biomolecule, such as DNA, RNA, lipid or sugar), a detectable label (e.g. fluorophore, imaging label or the like), a property modifying moiety (e.g. PEGylation moiety), a sulfhydryl-specific functional moiety such as a maleimide, alkyl or aryl halide, α-haloacyl, or pyridyl disulfides, an amine-specific functional moiety such as a carbodiimide, a non-selective reactive moiety such as a photoaffinity group, an arginine-specific functional moiety such as a glyoxal, etc.

The term "click chemistry" or "click reaction" refers to well-known, selective methods of conjugation, wherein two components comprising a click reactive functional group are reacted to link the two components. For example, for the sulfimide modified peptides, polypeptides or proteins as described herein, the modified group further comprises a first click reactive functional group, and the payload molecule is suitably modified to comprise a second click reactive functional group, which is reactive with the first click reactive functional group. The click reactive functional group includes, without limitation, an azide group, a nitrone group or an alkyne group. In some embodiments click chemistry comprises reaction of an azide group with an alkyne group to form a triazole group linking the two components, or the reaction of a nitrone group with an alkyne group to form an isoxazoline group linking the two components. In some embodiments, the alkyne group is a dibenzocyclooctyne (DBCO) group or a difluorooctyne (DIFO) group. In some embodiments, the click chemistry is Copper(I)-catalyzed azide-alkyne cycloaddition (CuAAC), strain-promoted azide-alkyne cycloaddition (SPAAC) or strain-promoted alkyne-nitrone cycloaddition (SPANC). See also Jewett, John C. and Bertozzi, Carolyn, R., Cu-free click cycloaddition reactions in chemical biology. Chem Soc Rev. 39(4), 1272-1279 (2010); Agard et al., A Comparative Study of Bioorthogonal Reactions with Azides. ACS Chem. Biol., 1(10), 644-648 (2006); MacKenzie et al., Strain-promoted cycloadditions involving nitrones and alkynes—rapid tunable reactions for biorthogonal labeling. Current Opinion in Chemical Biology 21, 81-88 (2014), the disclosures of which are hereby incorporated by reference in their entirety.

TABLE I

| Compounds | |
|---|---|
|  | 1 |
| 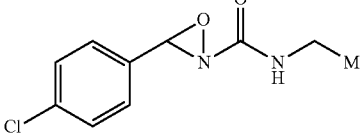 | 2 |
| 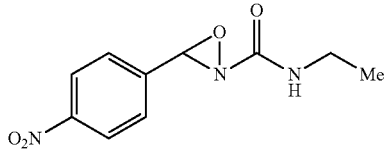 [SMILES: CCNC(=O)N1OC1c1ccc([N+](=O)[O-])cc1] | 3 |
| 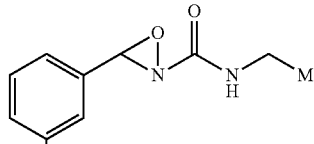 | 4 |
| 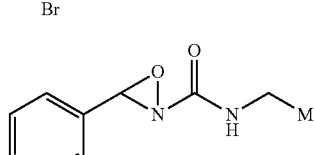 | 5 |
| 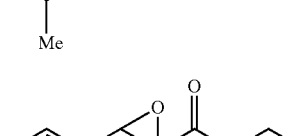 | 6 |

TABLE I-continued

| Compounds | |
|---|---|
| 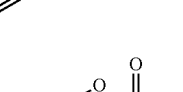 | 7 |
| 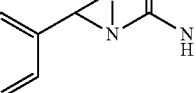 | 8 |
| 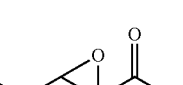 | 9 |
|  | 10 |
| 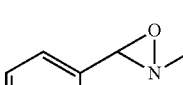 | 11 |
| 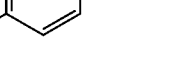 | 12 |
| 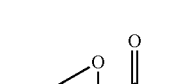 | 13 |
| 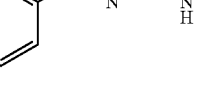 | 14 |
| 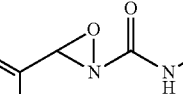 | 15 |

TABLE I-continued
Compounds
| | |
|---|---|
| 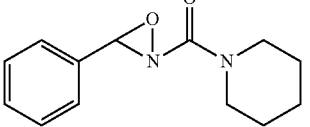 | 16 |
| 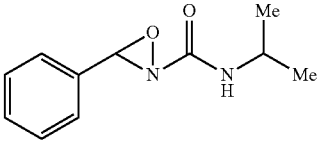 [SMILES: CC(C)NC(=O)N1OC1c1ccccc1] | 17 |
| 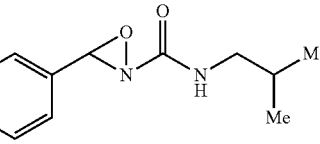 | 18 |
| 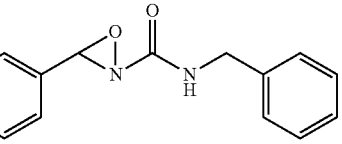 | 19 |
| 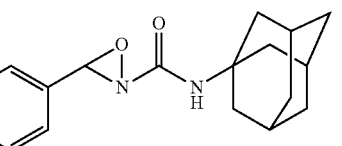 | 20 |
| 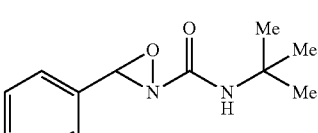 | 21 |
| 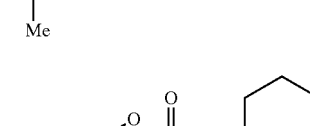 | 22 |
| 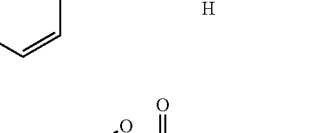 | 23 |
| 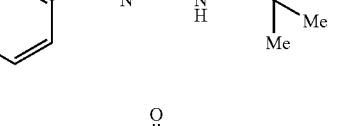 | 24 |
| 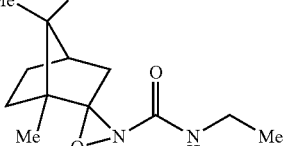 | 25 |
| 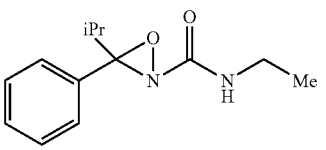 [SMILES: CCNC(=O)N1OC1(c1ccccc1)C(C)C] | 26 |
| 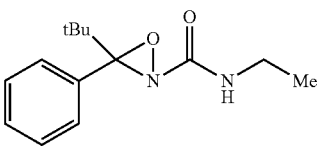 [SMILES: CCNC(=O)N1OC1(c1ccccc1)C(C)(C)C] | 27 |
| 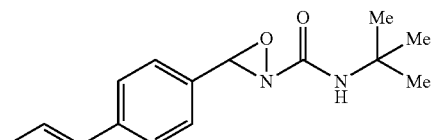 | 28 |
| 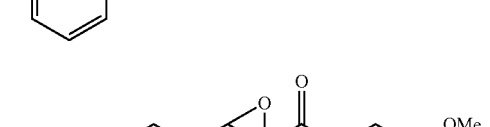 | 29 |
| 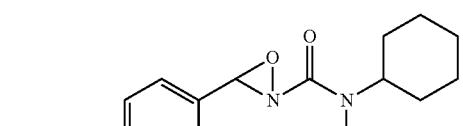 | 30 |
|  | 31 |
| 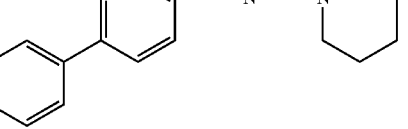 | 32 |

TABLE I-continued

Compounds

TABLE I-continued

Compounds

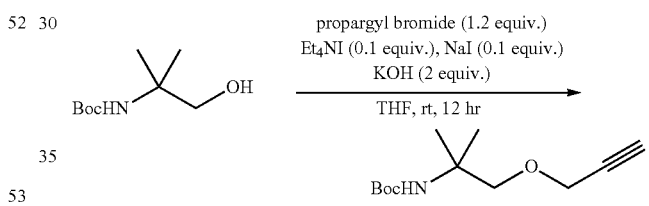

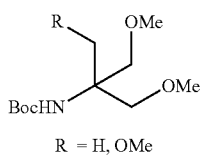

R = H, OMe

General Procedure for O-methylation: Tetramethyloxonium tetrafluoroborate (3 equiv.) and 1,8-Bis(dimethylamino)naphthalene (3 equiv.) were suspended in dry DCM (1.5 M) in a three-neck, flame-dried round bottom equipped with a reflux condenser under a positive pressure of N2. Previously reported N-boc amines (1 equiv.)1,2 were dissolved in dry DCM (0.5 M) and were added to the mixture in the round bottom flask. The mixture was refluxed for 36 hours or until starting material consumption was observed by thin-layer chromatography. The reaction was cooled to room temperature and was diluted with DCM (3× original volume). The organic layer was washed with sat. NaHCO3 (3×), brine (1×), dried over Na2SO4, and was concentrated under reduced pressure. The crude mixture was purified by column chromatography to afford pure N-boc, O-methyl amine.

Synthesis of N-Boc Amine Precursor for 40

[Reaction scheme: BocHN-C(Me)2-CH2-OH + propargyl bromide (1.2 equiv.), Et4NI (0.1 equiv.), NaI (0.1 equiv.), KOH (2 equiv.), THF, rt, 12 hr → BocHN-C(Me)2-CH2-O-CH2-C≡CH]

Previously reported N-boc amine (3.8 g, 20 mmol, 1 equiv.)3, propargyl bromide (80% in toluene) (2.7 mL, 24 mmol, 1.2 equiv.), tetraethylammonium iodide (510 mg, 2 mmol, 0.1 equiv.), and sodium iodide (300 mg, 2 mmol, 0.1 equiv.) were suspended in THF (100 mL, 0.2 M) in a flame-dried, three-neck round bottom flask under a positive pressure of N2. KOH (2.2 g, 40 mmol, 2 equiv.) was added portionwise (4×) every 20 minutes and was stirred at room temperature for 12 hours. The reaction was quenched with H2O (2× reaction volume), extracted with ethyl acetate (3×), dried over Na2SO4, and was concentrated under reduced pressure. The crude mixture was purified by column chromatography (20% ethyl acetate in hexanes) to afford pure product as a colorless oil (3.5 g, 77% yield).

Synthesis of Amine Precursor for 34, 35, 38-40

General Procedure for Boc Deprotection: N-boc amines (1 equiv.) were dissolved in MeOH (1 M), cooled to 0° C., and 4 M HCl in dioxane (2.2 equiv.) was added dropwise. The reaction was warmed to room temperature and was stirred until consumption of starting material was observed by thin-layer chromatography. The solution was concentrated under reduced pressure and the solid residue was washed with cold diethyl ether. The solid was used without future purification.

NOTE: N-boc amines for 384 and 405 were synthesized according to previously published procedures.

EXAMPLES

Compounds of Formula I, including compounds 11, 21, 23, 28, 33-35, 37-50

Synthesis of N-Boc Amine Precursor for 34 and 35

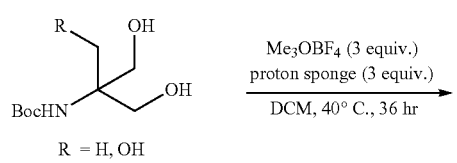

Me3OBF4 (3 equiv.)
proton sponge (3 equiv.)
DCM, 40° C., 36 hr

R = H, OH

Synthesis of Oxaziridines

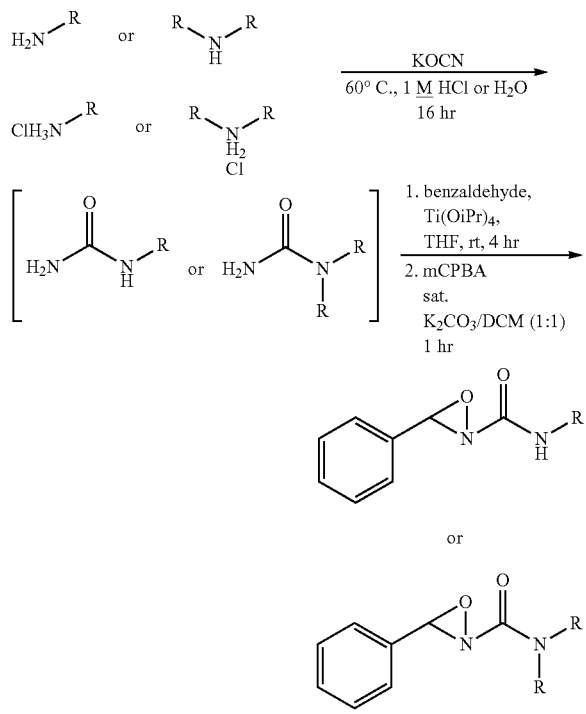

General Procedure for Urea Formation (Option 1—free amine): Amine (1 equiv.) was added to a 1 M HCl solution (1 mmol:1 mL). KOCN (3 equiv.) was added and the solution was stirred at 60° C. for 16 hours. The solution was cooled room temperature. If a precipitate formed: Solid was collected and washed with cold ethyl acetate, then pentane and was dried under reduced pressure to afford pure urea. If a precipitate did not form: Solution was concentrated under reduced pressure and residue was washed with EtOAc (500 mL for every 10 mmol of amine used), dried over Na2SO4, and was concentrated under reduced pressure to afford pure urea and was used in next step without further purification. *Do not use brine*

*Note: Depending on amine used, urea can be extremely soluble in water and sparingly soluble in EtOAc. Although we suggest using 500 mL for every 10 mmol, after concentration, if the yield is not suitable, we suggest more washings with EtOAc.

General Procedure for Urea Formation (Option 2—acid salt of amine): Amine (1 equiv.) was added H2O (1 mmol:1 mL). KOCN (3 equiv.) was added and the solution was stirred at 60° C. for 16 hours. The solution was cooled room temperature. If a precipitate formed: Solid was collected and washed with cold ethyl acetate, then pentane and was dried under reduced pressure to afford pure urea and was used in next step without further purification. If a precipitate did not form: Option A: Solution was concentrated under reduced pressure and residue was washed with EtOAc (500 mL for every 10 mmol of amine used), dried over Na2SO4, and was concentrated under reduced pressure to afford pure urea and was used in next step without further purification. Option B: Solution was extracted with EtOAc (5-10×, 500 mL total for every 10 mmol of amine used), dried over Na2SO4, and concentrated under reduced pressure to afford pure urea and was used in next step without further purification. *Do not use brine in either procedure*

*Note: This is the preferred method of urea formation for various reasons. First, if the amine being used needs to be synthesized, the resultant amine salt from a boc deprotection can be immediately used in this reaction without forming the free base. Secondly, this synthesis using Option B gives high yields (close to quantitative) compared to Option A or Option 1 (synthesis from free amine), especially when only using <20 mmol of the amine salt. Thus, this synthesis using Option B is generally preferred or if using precious amines. Option A is usually only preferred if original amine salt being used has functional groups that are especially polar and are hard to remove from water.

General Procedure for Oxaziridine Formation:

THF (30 mL) was added to urea (10 mmol, 1 equiv.) and aryl aldehyde (12 mmol, 1.2 equiv.) was subsequently added. Ti(OiPr)4 (14 mmol, 1.4 equiv.) was added and the reaction was stirred at room temperature for 4 hours. The solution was concentrated under reduced pressure and was used immediately.

*Note: The quality of Ti(OiPr)4 matters greatly in this reaction—our Ti(OiPr)4 is always kept under N2 after every use. If a considerable amount of solid (presumably TiO2) is in the bottle, it is suggested that a new bottle is used. Also, we have seen that the 4 hour condensation leads to the best yields but further reaction times can be necessary to facilitate further conversion. Conversion can be checked by taking an aliquot and observing benzaldehyde consumption using 1H NMR spectroscopy in toluene-d8.

mCPBA (75%, 30 mmol, 3 equiv.) was added to a 1:1 mixture of DCM:sat. K2CO3 (0.125 M) and was stirred for 10 minutes. Condensation residue (1 equiv.) was dissolved in DCM (1 M) and was added slowly to the mCPBA mixture. The mixture was vigorously stirred for 1 hour and was diluted with $H_2O$ (3× the volume). The biphasic solution was extracted with DCM (3×), the organic layer was washed with brine (1×), dried over Na2SO4, and was concentrated under reduced pressure. The concentrate was purified using column chromatography (1% Et2O in DCM) to afford the oxaziridine.

*Note: Sometimes multiple chromatographic steps are necessary to fully purify the oxaziridine. There are 3 options—1. Redo the 1% Et2O in DCM column (usually enough to purify most oxaziridines, typically used if the amide-urea or benzaldehyde are the impurities), 2. Do a column using EtOAc/hexanes as the eluent 3. Use reverse-phase chromatography (typically used if impurity has similar polarity/is co-polar with oxaziridine).

*For visualization of oxaziridine on TLC—phosphomolybdic acid (PMA) as a stain is highly recommended. Although oxaziridines can be visualized using UV, the spot typically does not appear unless the TLC plate is exposed for ~5 minutes to direct UV radiation and there will be multiple spots present try and deconvolute which spot is the oxaziridine (spot will also be very faint). To circumvent this hassle, PMA is recommended, as the oxaziridine spot turns a dark blue-green and is typically the only spot that appears.

Compounds of Formulas II and III, including compunds 9, 15-17, 30-31, 51-54

Synthesis of N-Boc Amine for 51

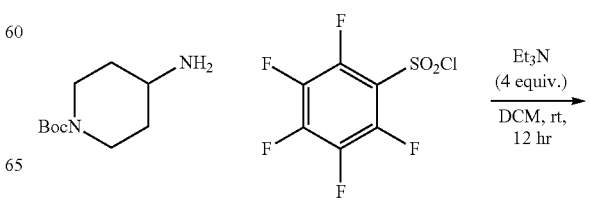

-continued

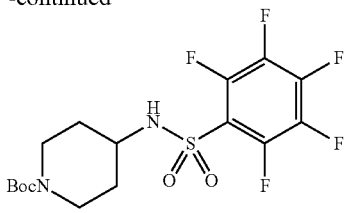

In a flame-dried, three-neck flask under N2, 4-amino, N-boc-piperidine (6.0 g, 30 mmol, 1 equiv.), triethylamine (18 mL, 120 mmol, 4 equiv.) were dissolved in DCM (150 mL, 0.2 M) and was cooled to 0° C. Pentafluorobenzenesulfonyl chloride (5.6 mL, 38 mmol, 1.25 equiv.) was added dropwise and the reaction was warmed to room temperature and was stirred overnight. The reaction was concentrated under reduced pressure and was purified by column chromatography (15% ethyl acetate in hexanes) to afford pure product (4.5 g, 35% yield).

Synthesis of Oxaziridines

General Procedure for Boc Deprotection: N-boc amines (1 equiv.) were dissolved in MeOH (1 M), cooled to 0° C., and 4 M HCl in dioxane (2.2 equiv.) was added dropwise. The reaction was warmed to room temperature and was stirred until consumption of starting material was observed by thin-layer chromatography. The solution was concentrated under reduced pressure and the solid residue was washed with cold diethyl ether. The solid was used without future purification.

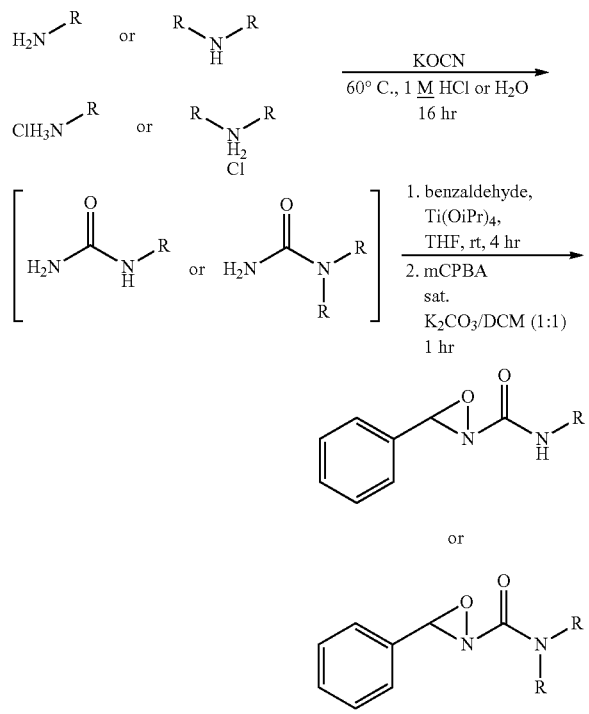

General Procedure for Urea Formation (Option 1—free amine): Amine (1 equiv.) was added to a 1 M HCl solution (1 mmol:1 mL). KOCN (3 equiv.) was added and the solution was stirred at 60° C. for 16 hours. The solution was cooled room temperature. If a precipitate formed: Solid was collected and washed with cold ethyl acetate, then pentane and was dried under reduced pressure to afford pure urea. If a precipitate did not form: Solution was concentrated under reduced pressure and residue was washed with EtOAc (500 mL for every 10 mmol of amine used), dried over Na2SO4, and was concentrated under reduced pressure to afford pure urea and was used in next step without further purification. *Do not use brine*

*Note: 1. Depending on amine used, urea can be extremely soluble in water and sparingly soluble in EtOAc. Although we suggest using 500 mL for every 10 mmol, after concentration, if the yield is not suitable, we suggest more washings with EtOAc. 2.

General Procedure for Urea Formation (Option 2—acid salt of amine): Amine (1 equiv.) was added H2O (1 mmol:1 mL). KOCN (3 equiv.) was added and the solution was stirred at 60° C. for 16 hours. The solution was cooled room temperature. If a precipitate formed: Solid was collected and washed with cold ethyl acetate, then pentane and was dried under reduced pressure to afford pure urea and was used in next step without further purification. If a precipitate did not form: Option A: Solution was concentrated under reduced pressure and residue was washed with EtOAc (500 mL for every 10 mmol of amine used), dried over Na2SO4, and was concentrated under reduced pressure to afford pure urea and was used in next step without further purification. Option B: Solution was extracted with EtOAc (5-10×, 500 mL total for every 10 mmol of amine used), dried over Na2SO4, and concentrated under reduced pressure to afford pure urea and was used in next step without further purification. *Do not use brine in either procedure*

*Note: This is the preferred method of urea formation for various reasons. First, if the amine being used needs to be synthesized, the resultant amine salt from a boc deprotection can be immediately used in this reaction without forming the free base. Secondly, this synthesis using Option B gives high yields (close to quantitative) compared to Option A or Option 1 (synthesis from free amine), especially when only using <20 mmol of the amine salt. Thus, this synthesis using Option B is generally preferred or if using precious amines. Option A is usually only preferred if original amine salt being used has functional groups that are especially polar and are hard to remove from water.

General Procedure for Oxaziridine Formation:

THF (30 mL) was added to urea (10 mmol, 1 equiv.) and aryl aldehyde (12 mmol, 1.2 equiv.) was subsequently added. Ti(OiPr)4 (14 mmol, 1.4 equiv.) was added and the reaction was stirred at room temperature for 4 hours. The solution was concentrated under reduced pressure and was used immediately.

*Note: The quality of Ti(OiPr)4 matters greatly in this reaction—our Ti(OiPr)4 is always kept under N2 after every use. If a considerable amount of solid (presumably TiO2) is in the bottle, it is suggested that a new bottle is used. Also, we have seen that the 4 hour condensation leads to the best yields but further reaction times can be necessary to facilitate further conversion. Conversion can be checked by taking an aliquot and observing benzaldehyde consumption using 1H NMR spectroscopy in toluene-d8.

*Note: For compound 53, a different procedure was used for the condensation. To a flame-dried three-neck flask equipped with a Dean-Stark trap and reflux condenser was added bis-urea (3.0 g, 10 mmol, 1 equiv.), benzaldehyde (2.6 mL, 25 mmol, 2.5 equiv.) pTsOH.H2O (370 mg, 2 mmol, 0.2 equiv.) and toluene (200 mL, 0.05 M). The solution was refluxed for 16 hours and the solution was concentrated under reduced pressure and residue was used crude.

mCPBA (75%, 30 mmol, 3 equiv.) was added to a 1:1 mixture of DCM:sat. K2CO3 (0.125 M) and was stirred for 10 minutes. Condensation residue (1 equiv.) was dissolved in DCM (1 M) and was added slowly to the mCPBA mixture. The mixture was vigorously stirred for 1 hour and was diluted with H$_2$O (3× the volume). The biphasic solution was extracted with DCM (3×), the organic layer was washed with brine (1×), dried over Na2SO4, and was concentrated under reduced pressure. The concentrate was purified using column chromatography (1% Et2O in DCM) to afford the oxaziridine.

*Note: Sometimes multiple chromatographic steps are necessary to fully purify the oxaziridine. There are 3 options—1. Redo the 1% Et2O in DCM column (usually enough to purify most oxaziridines, typically used if the amide-urea or benzaldehyde are the impurities), 2. Do a column using EtOAc/hexanes as the eluent 3. Use reverse-phase chromatography (typically used if impurity has similar polarity/is co-polar with oxaziridine).

*For visualization of oxaziridine on TLC—phosphomolybdic acid (PMA) as a stain is highly recommended. Although oxaziridines can be visualized using UV, the spot typically does not appear unless the TLC plate is exposed for ~5 minutes to direct UV radiation and there will be multiple spots present try and deconvolute which spot is the oxaziridine (spot will also be very faint). To circumvent this hassle, PMA is recommended, as the oxaziridine spot turns a dark blue-green and is typically the only spot that appears.

Procedures for compounds 25-27

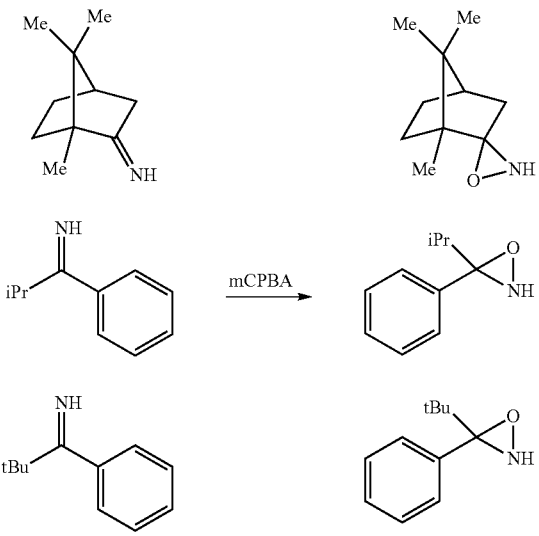

For compounds 26 & 27

A flame dried round-bottom flask was charged with benzonitrile (50.0 mmol) and THF (50 mL). The mixture was cooled to −78° C. and iPrLi or tBuLi (50.0 mL, 1.6 M in diethyl ether) was added dropwise over 1 h. The resulting mixture was stirred for 2 h and quenched with anhydrous ammonia in MeOH (12 mL, 4.0 M). The mixture was then stirred at rt for 2 hours.

The suspension was filtered on Celite and the filtrate was concentrated under vacuum. The crude material was taken on to the next step.

For compounds 25, 26 & 27.

A solution of m-CPBA (1.72 g, 1 equiv, 10 mmol) in dry dichloromethane (50 mL) was cooled to −40° C., leading to a heterogenous mixture. The reaction was kept stirring while a solution of the imine (10 mmol, 1 equiv) in dry dichloromethane (30 mL) was added to the mixture over a period of 4-5 minutes. The reaction was stirred overnight at −40° C. and allowed to reach room temperature. The reaction was stirred at room temperature for a further two hours. The solution was concentrated under reduced pressure, then 50 mL of diethyl ether was added. The precipitated m-chlorobenzoic acid was removed by filtration, and the rest was washed from the resulting solution with aqueous sodium hydroxide. The organic phase was dried with sodium sulfate, filtered, and concentrated under reduced pressure. The crude product was taken on to the next step.

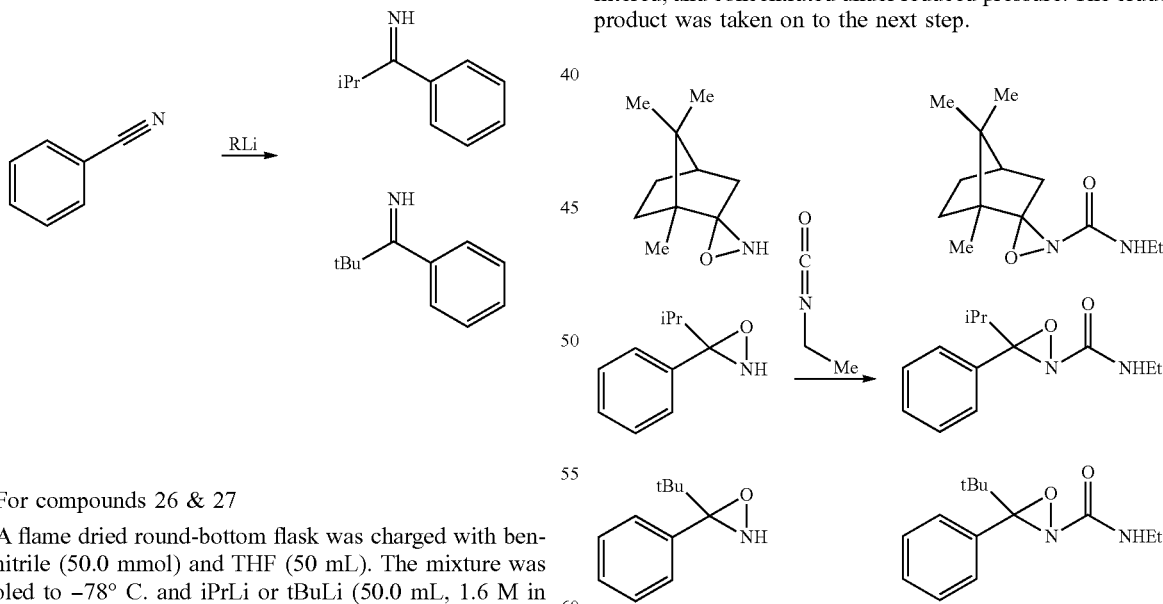

For compounds 25, 26 & 27.

A 1-dram vial was charged with the corresponding N—H oxaziridine (1 mmol), ethyl isocyanate (1.5 mmol), and dry toluene (2 mL). The reaction was let stirred overnight at room temperature. The solution was then concentrated under reduced pressure and purified by flash chromatography.

General Procedure for Coupling of Methionine and Oxaziridine

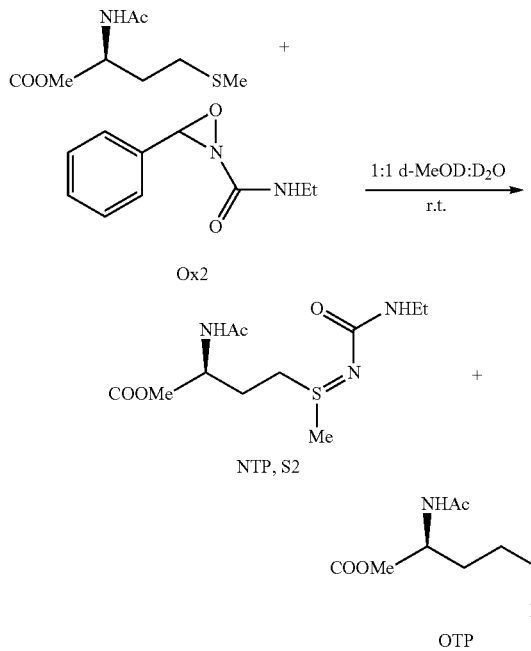

To a solution of methyl acetyl-L-methioninate (S1, 10.3 mg, 0.05 mmol) in d-MeOD/D$_2$O (0.25 mL/0.25 mL) was added oxaziridine Ox2 (10.6 mg, 0.055 mmol) at r.t. The conversion and ratio between NTP (S2) and OTP was monitored by $^1$H NMR. After 10 min, the solvents were removed under vacuum to give a residue, which was purified by column chromatography (DCM/MeOH, 5:1) to afford the S2 (13.2 mg, 91%) as an oil.

The Stability of Redox Conjugation Product-Sulfimide

The stability of sulfimides were tested by treatment of sulfimides S2 with 5 mM TCEP or treatment of sulfimides S3 with 1 N HCl, 1 N NaOH or 80° C. in co-solvent (d-MeOD/D2O=1:1). The reactions were monitored by NMR after 1 h and 18 h and the reaction conversions were calculated based on NMR data. Sulfimide S3 can be protonated under strong acidic condition to its salt form S4, which is stable in aqueous solution.

N-ethylcarbamyl-S-methyl-S-phenyl Sulfurimine (S3)

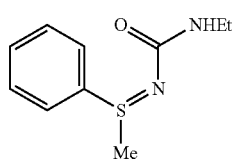

$^1$H NMR (500 MHz, MeOD) δ 7.81-7.75 (m, 2H), 7.62-7.54 (m, 3H), 3.18 (q, J=7.2, 5.9 Hz, 2H), 2.86 (s, 3H), 1.10 (t, J=7.2 Hz, 3H). $^{13}$C NMR (126 MHz, MeOD) δ 168.01, 139.36, 133.01, 130.91, 126.97, 36.78, 35.44, 15.89. m/z HRMS (ESI) found [M+H]$^+$ 211.0987, C$_{10}$H$_{15}$N$_2$OS$^+$ requires 211.0900.

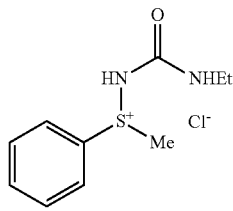

$^1$H NMR (400 MHz, MeOD/D$_2$O) δ 8.02 (d, J=7.5 Hz, 2H), 7.84 (t, J=7.4 Hz, 1H), 7.75 (t, J=7.7 Hz, 2H), 3.60 (s, 3H), 3.17 (q, J=7.2 Hz, 2H), 1.08 (t, J=7.2 Hz, 3H).

REFERENCES

Honjo, T.; Nakao, M.; Sano, S.; Shiro, M.; Yamaguchi, K.; Sei, Y.; Nagao, Y. Org. Lett. 2007, 9, 509-512

Das, R.; Mukhopadhyay, B. Tetrahedron Lett. 2016, 57, 1775-1781

Hunt, T.; Atherton-Watson, H. C.; Collingwood, S. P.; Coote, K. J.; Czarnecki, S.; Danahay, H.; Howsham, C.; Hunt, P.; Paisley, D.; Young, A. Bioorg. Med. Chem. Lett. 2012, 22, 2877-2879

Nishimura, H.; Kawai, H.; Nitta, A.; Oyama, T.; Kumagaya, H. Jpn. Kokai Tokkyo Koho 2010, JP 2010070514

Loskot, S. A.; Romney, D. K.; Arnold, F. H.; Stoltz, B. M. J. Am. Chem. Soc. 2017, 139, 10196-10199

The invention claimed is:

1. An N-transfer oxidant compound of formula III:

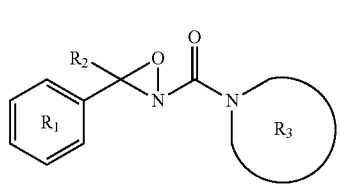

wherein:
R1 is optionally substituted C5, C6 or C8 aryl or heteroaryl;
R2 is H or optionally substituted C1-C6 alkyl; and
R3 is optionally substituted pyrrolidine or piperidine.

2. The compound of claim 1 wherein:
R1 is optionally substituted phenyl;
R2 is H; or
R3 is optionally substituted piperidine.

3. The compound of claim 1 wherein:
R1 is optionally substituted phenyl;
R2 is H; and
R3 is optionally substituted piperidine.

4. The compound of claim 3 wherein R3 is optionally para substituted piperidine.

5. The compound of claim 1 selected from:

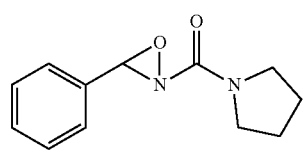

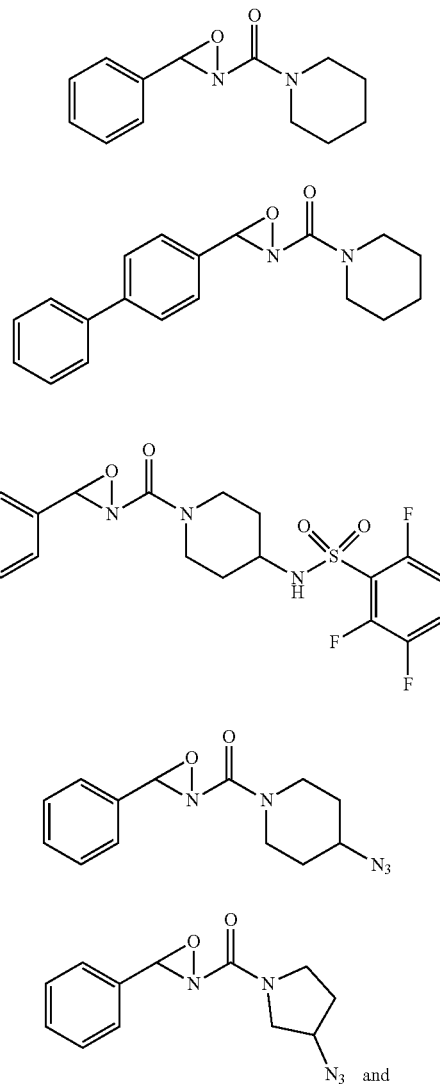

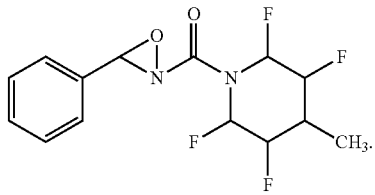

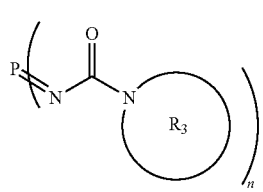

6. A method of chemoselective conjugation comprising reacting an N-transfer oxidant of claim 1 with a thioether substrate in an aqueous environment to form a conjugation product comprising a resultant sulfimide.

7. A sulfimide compound of formula IIIp:

IIIp wherein P represents a peptide or protein linked to the indicated nitrogen via a sulfimide bond with the sulfur of methionine, wherein the peptide or protein has n sulfimide modified methionine residues, where n is 1-20 and R3 is optionally substituted pyrrolidine or piperidine.

8. The method of claim 6, wherein the thioether substrate is a methionine, and the methionine is a residue in a peptide, polypeptide, or protein.

9. The method of claim 8, further comprising contacting the methionine-containing peptide, polypeptide or protein with an oxaziridine in an aqueous environment, wherein the oxaziridine directly functionalizes the peptide, polypeptide, or protein by converting at least one methionine of the peptide, polypeptide, or protein to the corresponding sulfimide conjugation product.

10. The method of claim 8, comprising stable isotope labeling with amino acid in cell culture (SILAC) or isotope coded affinity tag (ICAT).

* * * * *